United States Patent
Marsh et al.

(10) Patent No.: US 7,744,531 B2
(45) Date of Patent: Jun. 29, 2010

(54) METHOD FOR ASSESSING ADHESION OF SOILS OR EXUDATES TO THE SKIN

(75) Inventors: Randall Glenn Marsh, Hamilton, OH (US); Kristin Hofmann Miller, Springboro, OH (US); Andrea Dannenberg, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 428 days.

(21) Appl. No.: 11/807,289

(22) Filed: May 25, 2007

(65) Prior Publication Data

US 2007/0287986 A1    Dec. 13, 2007

Related U.S. Application Data

(60) Provisional application No. 60/812,782, filed on Jun. 12, 2006.

(51) Int. Cl.
*A61B 5/00* (2006.01)
(52) U.S. Cl. ........................ 600/306; 600/300
(58) Field of Classification Search .................. 600/306
See application file for complete search history.

(56) References Cited

U.S. PATENT DOCUMENTS

| 3,264,188 | A | | 8/1966 | Gresham |
| 4,613,447 | A | | 9/1986 | Hara et al. |
| 6,139,848 | A | * | 10/2000 | Ahmad et al. ............... 424/400 |
| 2003/0109811 | A1 | * | 6/2003 | Koenig et al. ............... 600/587 |
| 2005/0058833 | A1 | | 3/2005 | Krzysik et al. |

FOREIGN PATENT DOCUMENTS

| EP | 0 843 042 A1 | 5/1998 |
| EP | 0 957 201 A1 | 11/1999 |
| WO | WO 2005/110354 | 11/2005 |

OTHER PUBLICATIONS

International Search Report.

* cited by examiner

*Primary Examiner*—Robert L Nasser
*Assistant Examiner*—Michael D'Angelo
(74) *Attorney, Agent, or Firm*—Amy M. Foust; Laura L. Whitmer

(57) ABSTRACT

Method of assessing the adhesion of soils or exudates to the skin. The method may allow for an assessment of the amount of artificial bowel movement remaining on the skin following treatment with a lotion.

15 Claims, 3 Drawing Sheets

METHOD FOR ASSESSING ADHESION OF SOILS OR EXUDATES TO THE SKIN

CROSS-REFERENCE TO RELATED APPLICATIONS

This application claims the benefit of U.S. Provisional Application No. 60/812,782 filed on Jun. 12, 2006 which is incorporated herein by reference.

FIELD OF THE INVENTION

The present invention relates to a method for assessing the adhesion of soils or exudates to the skin. The method may allow for an assessment of the percent of artificial bowel movement remaining on skin.

BACKGROUND OF THE INVENTION

Cleaning the skin is a personal hygiene problem not always easily solved. Dry tissue products are the most commonly used cleansing products post-defecation, post-urination and during menstruation. Dry tissue products are also commonly used to remove soils, such as food and dirt, from the skin. Dry tissue products, such as those commonly used, are generally referred to as "toilet paper," "toilet tissue," or "paper towels." In addition to the use of dry tissue products, it is becoming increasingly frequent to use moistened substrates, such as wet wipes, for the purpose of cleansing the face and body after soiling, and the anus, the genital area, the perinea, and the peri-anal area after the voiding of bodily exudates. So called "wet wipes" are generally a fibrous structure impregnated with a water or oil-based lotion.

For the purpose of the present document, the anus, the perinea, the perineal area and the vulvar area are all terms indicating the body area of the pelvis between, around and including the anus and the external genitalia.

Both the perineal area and the vulvar area are marked by the presence of fine folds/wrinkles (sulci) and hair follicles, both of which make these regions more difficult anatomical areas to cleanse. During defecation, fecal matter is excreted through the anus and tends to accumulate in hard to reach locations such as around the base of hairs and in the sulci of the skin's surface. During menstruation, menses may accumulate on the skin and hair after the use of a sanitary napkin. As the fecal or menstrual matter dehydrates upon exposure to air or upon contact with an absorbent implement such as tissue paper, diaper, or sanitary napkin, it adheres more tenaciously to the skin and hair. Subsequent removal of the remaining dehydrated exudates may be even more difficult and may result in inadequate cleansing. Among those negatives associated with the failure of adequate cleansing are irritation, redness, desquamation, infections, unpleasant odor, or other kinds of personal discomfort or health related issues.

People suffering from pathological conditions (such as hemorrhoids, fissures, cryptitis, etc.) are even more susceptible to the negatives listed above. Common hygienic concerns make the benefits of a good cleansing after defecation, menstruation, and urination very relevant to babies, toddlers, children and adults. Cleansing must be efficient in terms of removal of residues and gentle in terms of absence of irritation caused by the cleansing. Wet-wipes bring a response to that basic need.

In comparison to dry tissue products, wet wipes have several benefits including:
  The enabling of a better lubrication during the use of the wipe, thereby reducing the abrasiveness of the cleansing operation;
  The hydration of the residues, thus enhancing their removal from the skin or hair;
  The hydration of the skin tissue; and
  The ability to deliver a soothing or protective lotion to the skin that can remain on the skin after the cleansing operation.

Manufacturers of wet wipes have tried to develop wipes products that deliver the right balance between normally antagonistic concepts such as:
  Enhancing the removal of soil while protecting the skin from irritation and abrasion.
  The long lasting feeling of comfortable cleanliness while avoiding a greasy feeling on the skin.

A variety of methods exist that may measure the strength of adhesion between two materials and that may ascertain whether or not the strength of the adhesive interactions between the two materials may be impacted by surface treatments or other factors such as temperature or relative humidity. Many of the methods may be intended for industrial or academic applications where the materials being studied generally may be non-biological, for example metals, woods, or polymers. For example, ASTM D2919 and ASTM D3528 determine the durability of adhesive joints stressed under shear. Other methods, such as those described in Adhesion Measurements of Films and Coatings edited by K. L. Mittal published in 1995 as available from VSP Publishers, may be useful for assessing the force required to peel a material away from a surface. Again, these methods may be generally intended for non-biological materials. Thus, there is the need for a method that may assess the strength of adhesion between a material and a biological surface. There exists a need for a method that may assess the strength of adhesion between soils or exudates and the skin surface.

SUMMARY OF THE INVENTION

A method to assess the percent residual artificial bowel movement on skin comprising the steps of applying said artificial bowel movement to said skin, applying weigh paper to said artificial bowel movement and removing said weigh paper. The method may further comprise the step of applying about 0.5 psi of a downward force to said weigh paper. The skin may be treated with a lotion.

The percent residual artificial bowel movement remaining on the skin may be calculated as a comparison of artificial bowel movement initially applied to the skin and artificial bowel movement associated with the weigh paper.

At least two different lotions may be applied to the skin to assess any difference between the percent residual artificial bowel movement remaining on the skin after application of each of the applied lotions.

A method to assess a change in the amount of adhesion of artificial bowel movement to skin comprising the step of comparing a percent of the artificial bowel movement remaining on non-lotion treated skin to a percent of the artificial bowel movement remaining on lotion treated skin.

DETAILED DESCRIPTION OF THE INVENTION

Figure 1:
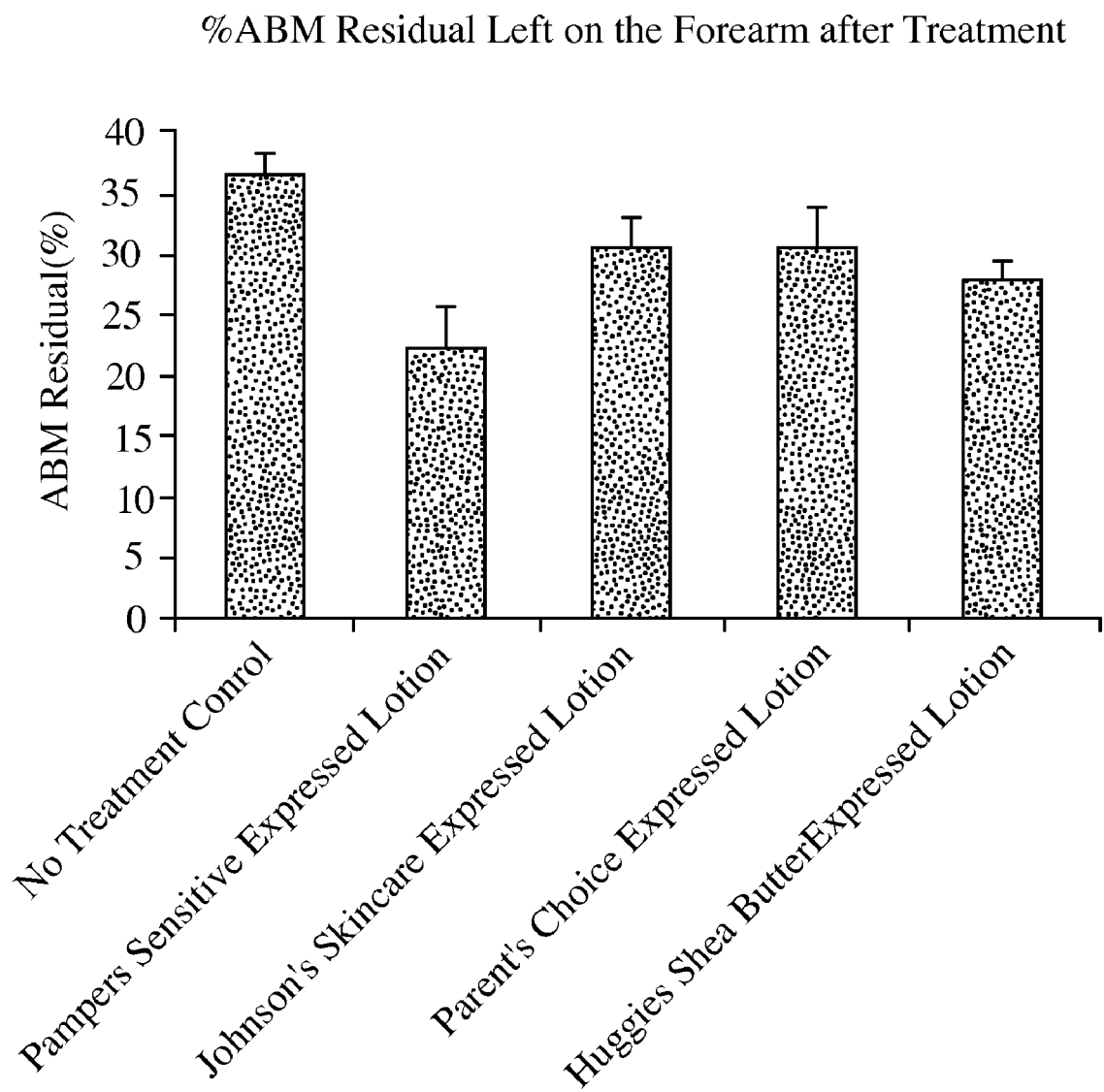
FIG. 1 is an example of the percent of artificial bowel movement residual left on a forearm following anti-stick treatment as demonstrated by the Anti-Stick Screening Method.
Figure 2:
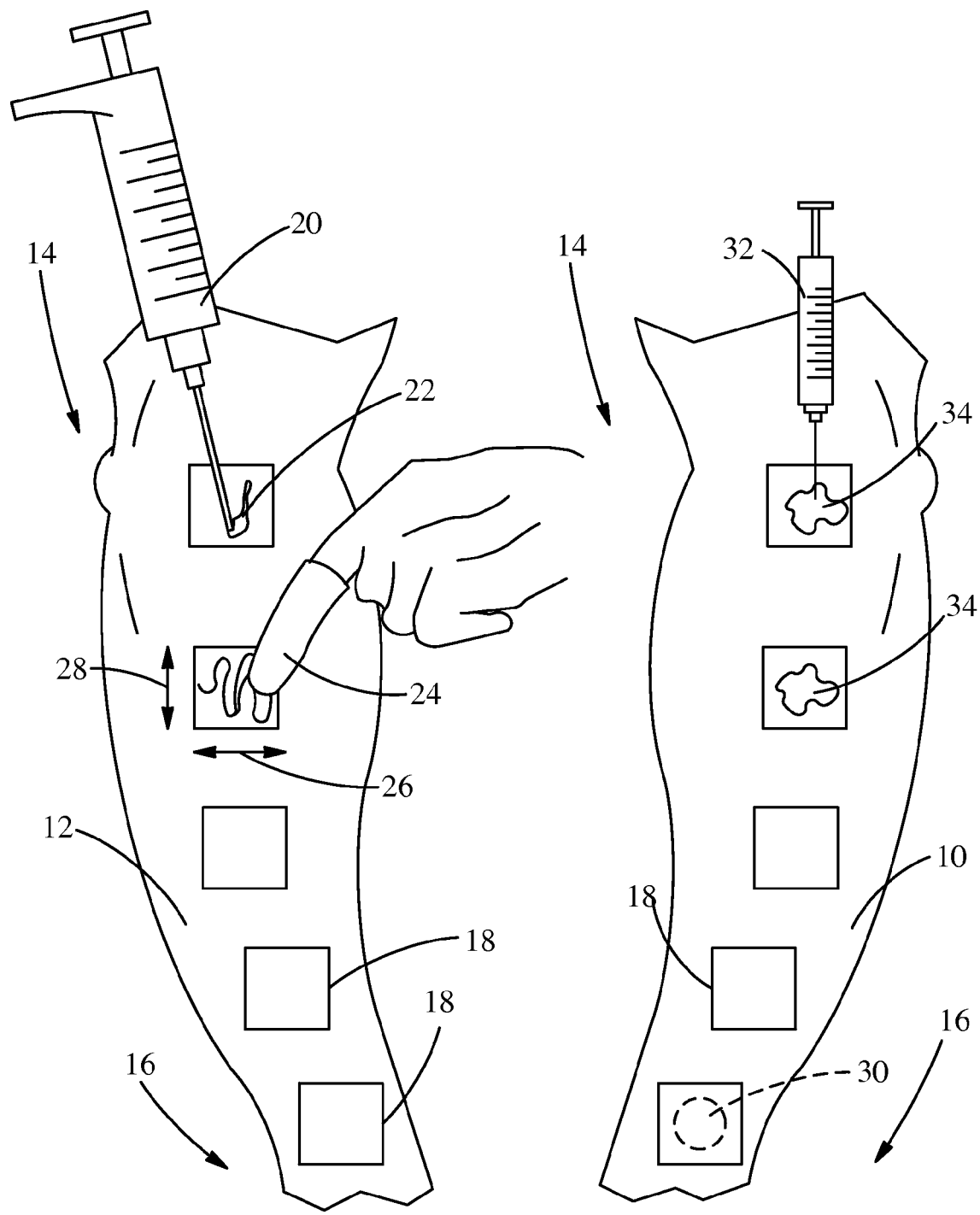
FIG. 2 is a perspective view of the volar forearms, showing exemplary test sites and test site preparation.
Figure 3A:
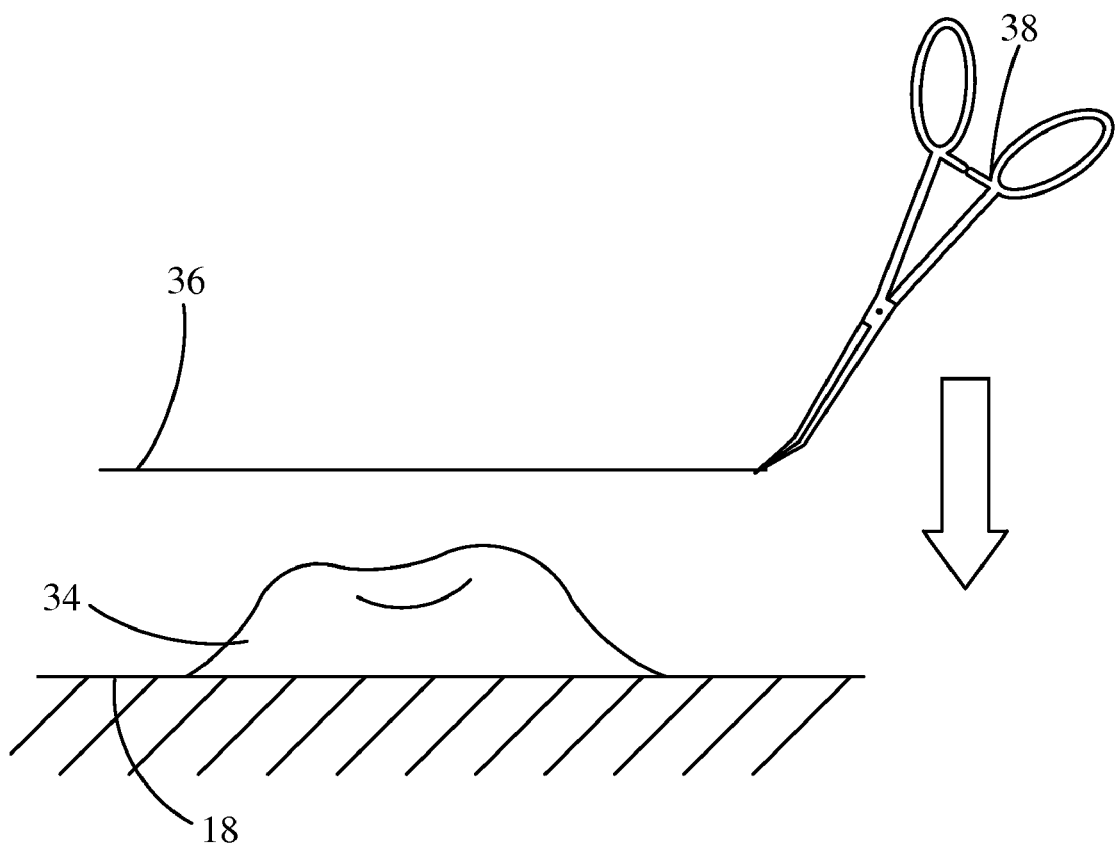
FIG. 3A is a side view of the application of a test paper to a test site.
Figure 3B:
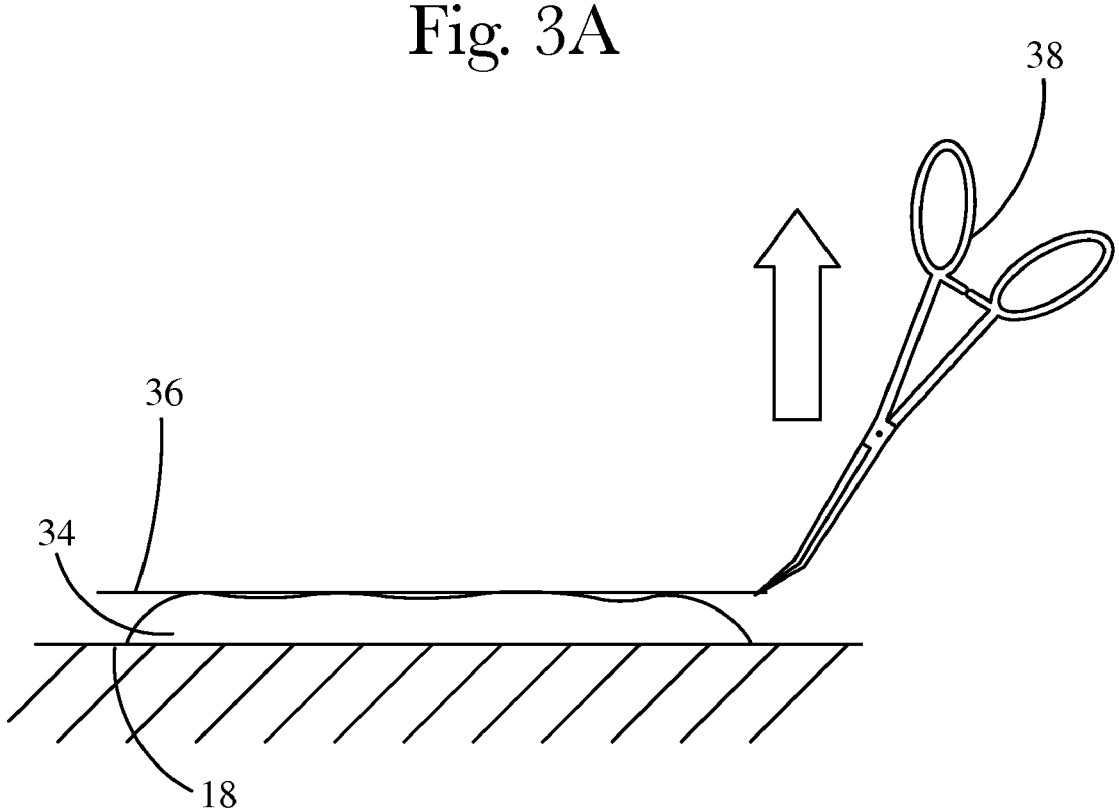
FIG. 3B is a side view of the removal of a test paper from a test site.
Figure 1:
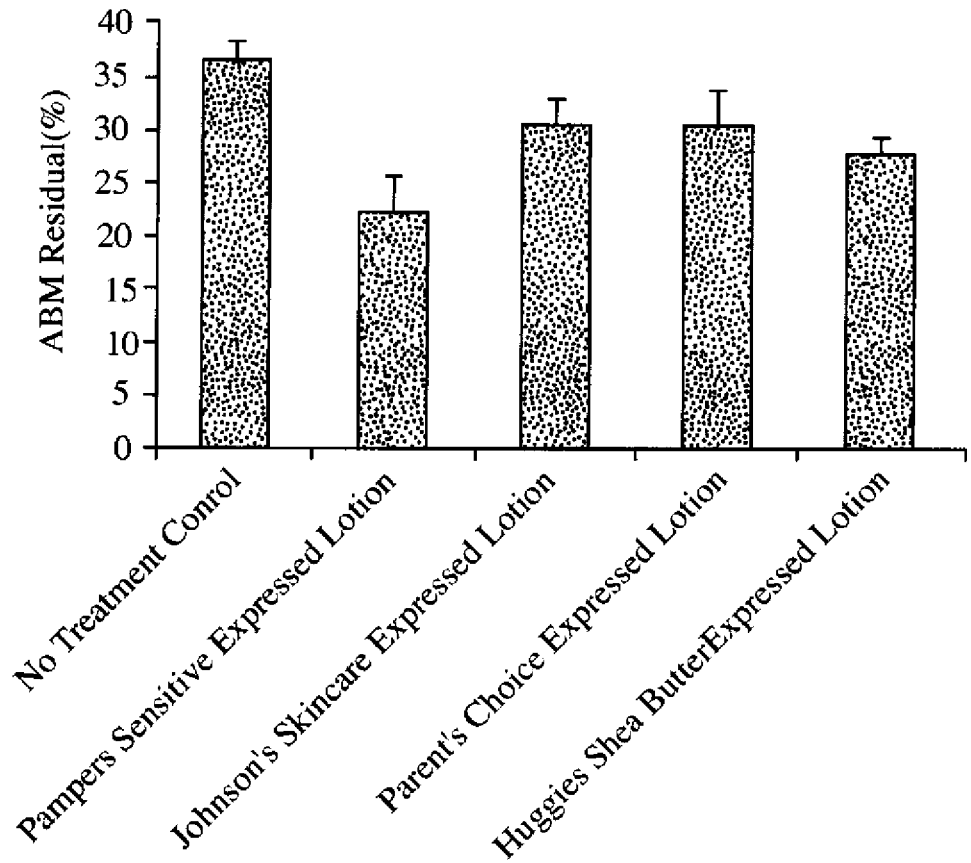

The ease with which soils or bodily exudates are removed from the skin may be related to the strength of the adhesive interactions between the soils or exudates and the skin surface. "Soils" refers herein to material from a source extraneous to the body, such as dirt and food. "Exudates" refers herein to material from a source internal to the body, such as urine, menses, feces, and mucus. As defined herein, "weight/weight" or "w/w" refers to the weight of the component being referenced versus the weight of the total material in reference. The use of "w/w" for residual artificial bowel movement (ABM) refers to the weight of the remaining artificial bowel movement on the skin versus the total weight of the artificial bowel movement applied to the skin.

Adhesion Screening Method

The strength of adhesion between two materials may be analyzed in a variety of methods to determine whether or not the adhesive interactions are impacted by surface treatments or other factors. Examples of adhesion tests for determining if a treatment has reduced adhesion between two materials (such as by reducing the force of adhesion to less than the force of cohesion) include ASTM D2919, ASTM D3528 and related methods referred to or described therein. Such methods may test the strength of adhesion through the application of shear.

A method for assessing the adhesion of soils or exudates to the skin surface has been detailed herein. This method is used for assessing the adhesion of soils or exudates to the skin by quantifying the amount of residual artificial pasty bowel movement ("ABM") left on the skin surface after treatment. While artificial ABM is utilized in the Adhesion Screening Method, the artificial ABM may correlate in physical properties to soils or exudates. The percent residual artificial ABM may, therefore, be utilized as an equivalent measurement of the percent residual soils or exudates.

Briefly, the Adhesion Screening Method treats the skin surface with a defined amount of a lotion 22. A defined amount of an artificial pasty bowel movement ("ABM") 34 is applied, covered with a square piece of paper 36, and compressed with a defined force for a defined amount of time. The paper 36 is then peeled away slowly with forceps 38. The paper 36 is tared before application of the ABM 34 and is re-weighed after removal from the skin. The percent residual ABM on the skin is calculated by mass balance. The ABM 34, similar to real infant BM, fails cohesively, resulting in part of the ABM 34 remaining on the skin surface and part of the ABM 34 remaining on the piece of paper 36. The more efficient the lotion 22, the less residual ABM on the skin surface.

At least eight healthy adults participate in a single screening study. Each of the panelists completes a four-day washout period during which they use Olay® unscented moisturizing soap, as distributed by The Procter and Gamble Company, Cincinnati, Ohio, to wash their forearms. Panelists must refrain from using any topical product, such as ointments, creams or lotions, on their forearms during this washout-out period and also on the day of the screening study. On the day of testing, panelist's arms are inspected to ensure they are free of cuts, scratches, and rashes. If any skin abnormalities are present, the panelist cannot participate.

A template and a fine-tip marker are used to mark-off up to ten 3 cm×3 cm sites 18 on the volar forearms 10, 12, i.e. up to ten sites 18 per panelist.

All but one of these sites 18 are treated with a lotion 22. The remaining site receives no lotion treatment, i.e. serves as a negative control. The location of the various treatments, including the no-treatment site, may be randomized among the sites on each panelist. Testing starts at the site closest to the elbow 14 on the left arm 10 and, as testing on each site is completed, progresses to the site closest to the wrist 16 on the left arm 10, then to the site closest to the elbow 14 on the right arm 12, and finally to the site closest to the wrist 16 on the right arm 12. Testing on each site 18 requires approximately 4 minutes, for a total time per panelist of approximately 40 minutes.

For each site 18 that is treated, 1 µl/cm$^2$ or 9 µl/site of lotion 22 is applied in the center 30 of the site 18 using a standard or positive displacement pipettor 20. The lotion 22 is then spread over the entire site 18 (the boundary of which is defined by the marks made using the template) using a powder-free finger cot 24, Catalog # 56613-413 as available from VWR Scientific of West Chester, PA, by placing the finger cot 24 on top of the lotion 22 droplet and lightly rubbing the finger cot 24 over the skin surface using several side-to-side 26 and up-and-down 28 movements for a total elapsed time of 10-15 seconds. Examining the site 18 from an oblique angle, the person conducting the test may ensure that a uniform film has been formed over the entire area of the site 18. The film is left exposed to air, untouched, for approximately 1 minute prior to proceeding with the subsequent steps.

A 1 ml syringe 32, such as Catalog # BD-309628 as available from VWR Scientific of West Chester, PA, that has been filled with room temperature ABM 34 and is devoid of air bubbles, is placed onto a tared four-place analytical balance. The weight is recorded. The syringe 32 with ABM 34 is held over the center 30 of the test site 18 on the forearm 10, in reasonably close proximity to the skin surface, and approximately 0.2 ml of ABM 34 is dispensed onto the skin by pressing the plunger and by watching the gradations on the syringe 32. The ABM 34 should form a reasonably uniform, compact mound in the center 30 of the test site 18. The syringe 32 is re-weighed on the analytical balance, and the weight is recorded. The quantity of ABM 34 that was delivered to the forearm 10 is calculated by subtracting the second weight from the first weight.

A 4 cm×4 cm piece of weigh paper 36, Catalog # 12578-201 as available from VWR Scientific of West Chester, PA, is tared on the four place analytical balance, centered over the ABM 34 mound on the forearm test site 18, and gently lowered onto the ABM 34 using forceps 38. The weigh paper 36 must not be touched with fingertips, as this may transfer oils onto its surface. Next, a 500 g bottle-shaped weight, such as Catalog # 12766-518 as available from VWR Scientific of West Chester, PA, that exerts approximately 0.5 psi of downward force is placed over the weigh paper 36 such that the mound of ABM 34 under the weigh paper 36 is approximately centered under the weight. The weight may be gently held in place or balanced on the forearm by the panelist for 30 seconds. After 30 seconds have elapsed, two fingers are placed gently on either side of the weigh paper 36 to hold it in place, and the 500 g weight is slowly lifted. Using a pair of forceps 38, the weigh paper 36 is slowly and gently peeled from the test site. The forceps 38 are placed at the lower right corner of the weigh paper 36, and the weigh paper 36 is slowly peeled upwards in the direction of the upper left corner of the weigh paper 36. It should take approximately 1-2 seconds to remove the weigh paper 36. Once removed, the weigh paper 36 is placed back onto the analytical balance that it was tared on, and the weight is recorded to determine the amount of ABM 34 removed.

The above steps are repeated until all sites per panelist have been tested, i.e. the steps consisting of application of lotion 22, application of ABM 34, application of weigh paper 36, application of weight, and removal of weigh paper 36. For the no-treatment control, application of the lotion 22 is skipped and ABM 34 is applied directly to the skin site 18.

An example of a spreadsheet to collect the various weight measurements and to calculate the percent (%) residual ABM left on the arm may be as follows:

| Sub | Site | Trtmnt | Syringe | Syringe After | ABM Applied | ABM Removed | % ABM Arm |
|-----|------|--------|---------|---------------|-------------|-------------|-----------|
| 101 | 1    | I      | 7.8561  | 7.6351        | 0.2210      | 0.1678      | 24.07     |
| 101 | 2    | J      | 7.6343  | 7.4241        | 0.2102      | 0.1967      | 6.42      |
| 101 | 3    | H      | 7.4223  | 7.2208        | 0.2015      | 0.1473      | 26.90     |
| 101 | 4    | A      | 7.2200  | 7.0090        | 0.2110      | 0.1754      | 16.87     |
| 101 | 5    | G      | 7.0080  | 6.8087        | 0.1993      | 0.1755      | 11.94     |
| 101 | 6    | B      | 7.8082  | 7.5957        | 0.2125      | 0.2042      | 3.91      |
| 101 | 7    | F      | 7.5943  | 7.3862        | 0.2081      | 0.1536      | 26.19     |
| 101 | 8    | C      | 6.9643  | 6.7592        | 0.2051      | 0.1526      | 25.60     |
| 101 | 9    | E      | 7.3840  | 7.1725        | 0.2115      | 0.1984      | 6.19      |
| 101 | 10   | D      | 7.1711  | 6.9678        | 0.2033      | 0.1788      | 12.05     |

Wherein:
Sub refers to the subject number, which is minimally 101 to 108 and ideally 101 to 110, i.e. the above chart would be replicated 8 to 10 times to cover all panelists.
Site refers to arm location, starting with the left arm near the elbow (Site 1) and proceeding to the right arm near the wrist (Site 10).
Trtmnt refers to the code of the treatment applied, typically a letter from A-J.
Syringe refers to the initial weight of the syringe containing ABM.
Syringe After refers to the final weight of the syringe containing ABM once approximately 0.2 ml of ABM has been dispensed onto a treatment site.
ABM Applied is a calculated value obtained from the equation Syringe−Syringe After=ABM Applied.
ABM Removed refers to the weight of the ABM that has been captured on the tared weight paper after the weigh paper has been peeled from a treatment site.
% ABM Arm is a calculated value obtained from the equation ((ABM Applied−ABM Removed)/ABM Applied)× 100. This is a measure of the percent (%) residual ABM on the skin surface after treatment.

The mean and standard error of the mean ("SEM") for each treatment, e.g. A-J, for all panelists, e.g. 101-110, is calculated and graphed. FIG. 1 is an illustration of an example of the percent of artificial bowel movement residual left on a forearm following treatment. In FIG. 1, the grey bar represents the mean of each treatment. The error bar represents the SEM of each treatment. This example graph shows only five treatments for simplicity.

Preparation of Lotion

This method may be used to assess expressed lotion compositions from any available wipe product. Expressed lotion compositions are prepared by inserting the entire wipe stack of a non-expired wet wipe product into a pre-cleaned press capable of exerting about 80 psi downward force on the stack. Ideally, the lower plate of the press contains a channel into which the expressed lotion may collect, and a hole through which the expressed lotion may flow into a clean storage container. An example of a suitable storage container is Catalog #83008-666 as available from VWR Scientific of West Chester, Pa. All expressed lotions are stored at room temperature prior to use.

On the day prior to the study, 10 ml of each lotion is transferred into a glass scintillation vial such as Catalog #66022-060 as available from VWR Scientific of West Chester, Pa. Each vial is labeled with the treatment code, e.g. A-J. On the day of the study, the lotion is drawn from the scintillation vial with the standard or positive displacement pipettor and applied to the respective treatment site as described in the method. By having the various treatments in the scintillation vials, it is very easy to rearrange the vials in between panelists to accommodate the randomization scheme for the study.

To ensure reproducible results, the Adhesion Screening Method should be run at a room temperature of 21° C.±2° C. and at a relative humidity of 30-50%.

Preparation of Artificial Pasty Bowel Movement (ABM)
The following equipment is required:
an analytical balance accurate to ±0.001 g
a homogenizer capable of stirring the ingredients to homogeneity, such as an Ika Labortechnik™ T25 basic or equivalent as available from Ika-Werke GmbH and Co. KG of Staufen, Germany.
a homogenizer probe to be used with the homogenizer, such as Catalog #S25N 25F as available from Ika-Werke GmbH and Co. KG of Staufen, Germany.
The following reagents are required:
Feclone™ Powder #4, available from SiliClone Studio, Valley Forge, Pa., as Catalog Number Feclone BFPS-4.
Feclone™ Powder #6, available from SiliClone Studio, Valley Forge, Pa., as Catalog Number BFPS-6.
Feclonem Powder #7, available from SiliClone Studio, Valley Forge, Pa., as Catalog Number BFPS-7.
Carbopol™ 981, available from BF Goodrich, Cleveland, Ohio.
Deionized water.

The following quantities of the above reagents are required:

| Ingredient | Grams |
|------------|-------|
| Deionized water for Carbopol ™ solution | 78.78 |
| Feclone ™ powder #4 | 6.600 |
| Feclone ™ powder #6 | 6.600 |
| Feclone ™ powder #7 | 6.600 |
| Carbopol ™ 981 | 0.900 |

The procedure to prepare the ABM consists of the following steps:
A. Preparation of Carbopol™ Solution
1. Weigh 78.78 g±0.01 g of deionized water in a 250 ml beaker.
2. Weigh 0.900 g±0.001 g of Carbopol™ on weigh paper.
3. Put beaker on a magnetic stirrer and set speed at 400 rpm.
4. Add Carbopol™ powder slowly to the water, over the span of about 5 minutes. While adding the Carbopol™, increase the stirring speed slowly to 600 rpm.
5. Once the Carbopol™ powder has been added to the water, cover the beaker and continue mixing at 600 rpm for 15 minutes. The Carbopol™ powder must be completely dispersed, i.e. a transparent gel without any agglomerates.

6. Set up a hot plate at 150° C. Place the Carbopol™ solution on the hot plate and continue mixing at 600 rpm until the solution is heated to 81° C. to 83° C.

B. Preparation of ABM Mixture

1. Weigh 6.600 g±0.01 g each of Feclonem™ powders #4, #6, and #7 into a beaker and mix well.
2. Using a T25 basic or equivalent homogenizer with a homogenizer probe, stir the Carbopol™ solution at 8000 rpm for about 30 seconds before proceeding with Step 3.
3. To the Carbopol™ solution that is being stirred, slowly add the Feclonem powder mixture, about one quarter of the total at a time. Ensure that the Feclone™ powder mixture gets pulled through the homogenizer probe during addition, i.e. is thoroughly mixed into the pasty composition that is forming. If necessary, use a spatula to facilitate incorporation of the Feclone™ powder mixture into the composition.
4. After all of the Feclone™ powder mixture has been added, continue mixing with the homogenizer at 8000 rpm for an additional 5 minutes, using the spatula to push the pasty composition towards the homogenizer probe. The composition should be thoroughly mixed and appear homogeneous.

The finished ABM may be placed in a container, such as Catalog #14233-954 as available from VWR Scientific of West Chester, Pa., and stored in the refrigerator for up to 30 days. After 30 days, a new sample should be prepared for further experiments. The container must be tightly sealed to avoid drying out of the ABM.

Prior to using the ABM in the Adhesion Screening Method, the ABM must be removed from the refrigerator and allowed to adjust back to room temperature. An easy way to accomplish this is to fill a 10 ml syringe, such as Catalog #BD301604 as available from VWR Scientific of West Chester, Pa., with cold ABM and then allow the syringe to equilibrate to room temperature on a counter top. Equilibration typically takes about 15 minutes. The 10 ml syringe can then be used to fill the 1 ml syringe described in the Adhesion Screening Method.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method to assess artificial bowel movement removal from skin comprising the steps of:
    a. applying the artificial bowel movement to the skin;
    b. applying weigh paper to the artificial bowel movement;
    c. using the weigh paper to remove at least a portion of the artificial bowel movement by slowly peeling the weigh paper upwards, from a first corner of the weigh paper toward a second corner diagonally opposite the first corner; and
    d. weighing the weigh paper to determine the amount of artificial bowel movement associated with the weigh paper.

2. The method of claim 1 further comprising the step of applying about 0.5 psi of downward force to the weigh paper.

3. The method of claim 2 wherein the downward force is applied for a duration of about 30 seconds.

4. The method of claim 1 wherein about 0.2 ml of artificial bowel movement is applied to the skin.

5. The method of claim 1 wherein the skin is treated with a lotion.

6. The method of claim 5 wherein the skin is treated with the lotion prior to the application of the artificial bowel movement.

7. The method of claim 5 wherein the skin is treated with about 1 μ/cm$^2$ of the lotion.

8. The method of claim 5 wherein at least two different lotions are applied to the skin to assess the artificial bowel movement removal from skin after application of each of the lotions.

9. The method of claim 8 wherein each of the lotions is applied to a different test site on the skin.

10. A method to assess artificial bowel movement removal from skin comprising the steps of:
    a. applying a lotion to the skin;
    b. applying the artificial bowel movement to the skin;
    c. applying weigh paper to the artificial bowel movement;
    d. applying about 0.5 psi of a downward force to the weigh paper;
    e. using the weigh paper to remove at least a portion of the artificial bowel movement by slowly peeling the weigh paper upwards, from a first corner of the weigh paper toward a second corner diagonally opposite the first corner; and
    f. weighing the weigh paper to determine the amount of artificial bowel movement associated with the weigh paper.

11. The method of claim 10 wherein the skin is treated with about 1 μ/cm$^2$ of the lotion.

12. The method of claim 10 wherein the artificial bowel movement is applied to the lotion-treated skin.

13. The method of claim 10 wherein the downward force is applied for a duration of about 30 seconds.

14. The method of claim 10 wherein at least two different lotions are applied to the skin to assess the artificial bowel movement removal from skin after application of each of the lotions.

15. The method of claim 14 wherein each of the lotions is applied to a different test site on the skin.

* * * * *

UNITED STATES PATENT AND TRADEMARK OFFICE
CERTIFICATE OF CORRECTION

PATENT NO.        : 7,744,531 B2  
APPLICATION NO.   : 11/807289  
DATED             : June 29, 2010  
INVENTOR(S)       : Marsh et al.

Page 1 of 2

It is certified that error appears in the above-identified patent and that said Letters Patent is hereby corrected as shown below:

Drawings
Fig. 1, under the bar on the far left, delete "No Treatment Conrol" and insert --No Treatment Control-- on attached page.

Column 6
Line 38, delete "Feclonem" and insert --Feclone™--.

Column 7
Line 14, delete "Feclonem" and insert --Feclone™--.

Column 8
Line 29, delete "1 µ/cm$^2$" and insert --1 µl/cm$^2$--.
Line 52, delete "1 µ/cm$^2$" and insert --1 µl/cm$^2$--.

Signed and Sealed this
Twenty-fifth Day of January, 2011

David J. Kappos
*Director of the United States Patent and Trademark Office*